(12) United States Patent
Han et al.

(10) Patent No.: US 6,408,050 B1
(45) Date of Patent: Jun. 18, 2002

(54) X-RAY DETECTOR AND METHOD FOR TISSUE SPECIFIC IMAGE

(75) Inventors: Sung Su Han, Niskayuna, NY (US); Paul Richard Granfors, Sunnyvale, CA (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 51 days.

(21) Appl. No.: 09/661,776

(22) Filed: Sep. 14, 2000

(51) Int. Cl.[7] .................................................. H05G 1/64
(52) U.S. Cl. ..................................... 378/98.9; 378/98.11
(58) Field of Search ................................. 378/98.9, 98.11

(56) References Cited

U.S. PATENT DOCUMENTS 5,742,658 A * 4/1998 Tiffin et al. .................... 378/44

OTHER PUBLICATIONS

"Active Dual Energy X–Ray Detector: Experimental Characterization", Alvarez et al., Medical Imaging 1997: Physics of Medical Imaging, May 12, 1997, p. 419–426.

"Experimental Comparison of Dual Energy X–ray Detectors", Alvarez et al., Medical Imaging 1996: Physics of Medical Imaging, May 7, 1996, p. 534–543.

"Generalized Image Combinations in Dual KVP Digital Radiography", Lehmann et al., Medical Physics, vol. 8, No. 5, Sep./Oct. 1981, p. 659–667.

"Single–Exposure Dual–Energy Computed Radiography", Stewart et al., Medical Physics, vol. 17, No. 5, Sep/Oct. 1990, p. 866–875.

* cited by examiner

Primary Examiner—Robert H. Kim
Assistant Examiner—Courtney Thomas
(74) Attorney, Agent, or Firm—McAndrews, Held & Malloy, Ltd.; Peter J. Vogel; Michael A. Dellapenna

(57) ABSTRACT

A method for energy dependent imaging of a region of interest includes the step of exposing an X-ray detector to X-ray photons during an examination period, and separating the X-ray photons into two groups, those with energies above a selected energy threshold, and those with energies below a selected energy threshold. The X-ray photons with energy above the threshold are counted to provide a first energy photon count, while the X-ray photons with energy below the threshold are counted to provide a second energy photon count. The method stores the first energy photon count and the second energy photon count in a memory as examination data, and produces an image by applying an image processing technique to the examination data.

20 Claims, 4 Drawing Sheets

X-RAY DETECTOR AND METHOD FOR TISSUE SPECIFIC IMAGE

BACKGROUND OF THE INVENTION

The present invention relates to medical diagnostic X-ray imaging. In particular, the present invention relates to photon counting and energy discrimination to image selected and specific types of tissue or other structure.

Today, doctors and technicians commonly have access to very sophisticated medical diagnostic X-ray imaging devices. Typically during the operation of an X-ray imaging device, an X-ray source emits X-ray photons under very controlled circumstances. The X-ray photons travel through a region of interest (ROI) of a patient under examination and impinge upon a detector. In the past, X-ray imaging devices employed rudimentary film based detectors. However, recent developments have led to solid state detectors comprised of a grid of discrete detector elements that individually respond to exposure by X-ray photons. Regardless of the detector used, however, the goal remains the same, namely, to produce a clear resultant image of preselected structures of interest (e.g., specific types of tissues) within the ROI.

There is an inherent difficulty associated with producing a clear resultant image, however. In particular, because the X-ray photons travel through the entire patient, the image formed on the detector is a superposition of all the anatomic structures through which X-ray photons pass, including the preselected structures of interest. The superposition of anatomic structures is sometimes referred to as "anatomic noise". The effect of anatomic noise on the resultant image is to produce clutter, shadowing, and other obscuring effects that render the resultant image much less intelligible than the ideal clear resultant image.

Past attempts to reduce the effects of anatomic noise included, for example, "dual-energy" imaging. When employing dual-energy imaging, a doctor or technician acquired two images each with different average X-ray photon energies. Because different internal structures absorb different X-ray photon energies to different extents, it was possible to combine the two resultant images to suppress anatomic noise. Past dual-energy techniques typically proceeded in one of two ways.

A first approach used two stacked detectors. A single exposure then produced a first image in the first detector. Some X-ray photons continued through the first detector to impinge upon the second detector. The first and second detectors were designed to sense different average energies, thereby producing two images of the ROI corresponding to the two average X-ray photon energies. However, beyond the additional cost and complexity stemming from use of two stacked detectors, it was often difficult to obtain a large X-ray photon energy response separation between the two detectors. This caused the images produced by combining the two images using an algorithm designed to reduce anatomic noise to have poor contrast to noise ratio.

A second approach used a single detector and two exposures each with different average X-ray photon energy. Although this approach avoids the difficulties associated with the stacked detector, it suffers from its own problems. For example, patients often moved between exposures, thereby producing images of somewhat different internal structure between the two exposures. Furthermore, the X-ray source had to include additional circuitry to support selection of the specific X-ray photon energy to be produced.

A need has long existed in the industry for an imaging method that addresses the problems noted above and previously experienced.

BRIEF SUMMARY OF THE INVENTION

A preferred embodiment of the present invention provides, for an X-ray imaging system, a method for energy dependent imaging of a region of interest. The method includes the step of exposing an X-ray detector to X-ray photons during an examination period, and separating the X-ray photons into two groups, those with energies above a selected energy threshold, and those with energies below a selected energy threshold.

The X-ray photons with energy above the threshold are counted to provide a first energy photon count, while the X-ray photons with energy below the threshold are counted to provide a second energy photon count. The method stores the first energy photon count and the second energy photon count in a memory as examination data, and produces an image by applying an image processing technique to the examination data.

Another preferred embodiment of the present invention provides an X-ray imaging system adapted for energy dependent imaging of a region of interest. The imaging system includes an X-ray detector responsive to X-ray photons during an examination period, an X-ray energy photon discriminator (with a variable energy threshold control input) coupled to the X-ray detector, and a memory connected to a processor.

The memory stores instructions for execution by the processor for reading a first energy photon count of X-ray photons above a selected energy threshold, and for reading a second energy photon count of X-ray photons below the selected energy threshold. The memory also includes instructions that direct the processor to store the first energy photon count and the second energy photon count in the memory as examination data, and apply an image processing technique to the examination data to produce an image.

DETAILED DESCRIPTION OF THE INVENTION

Figure 1:
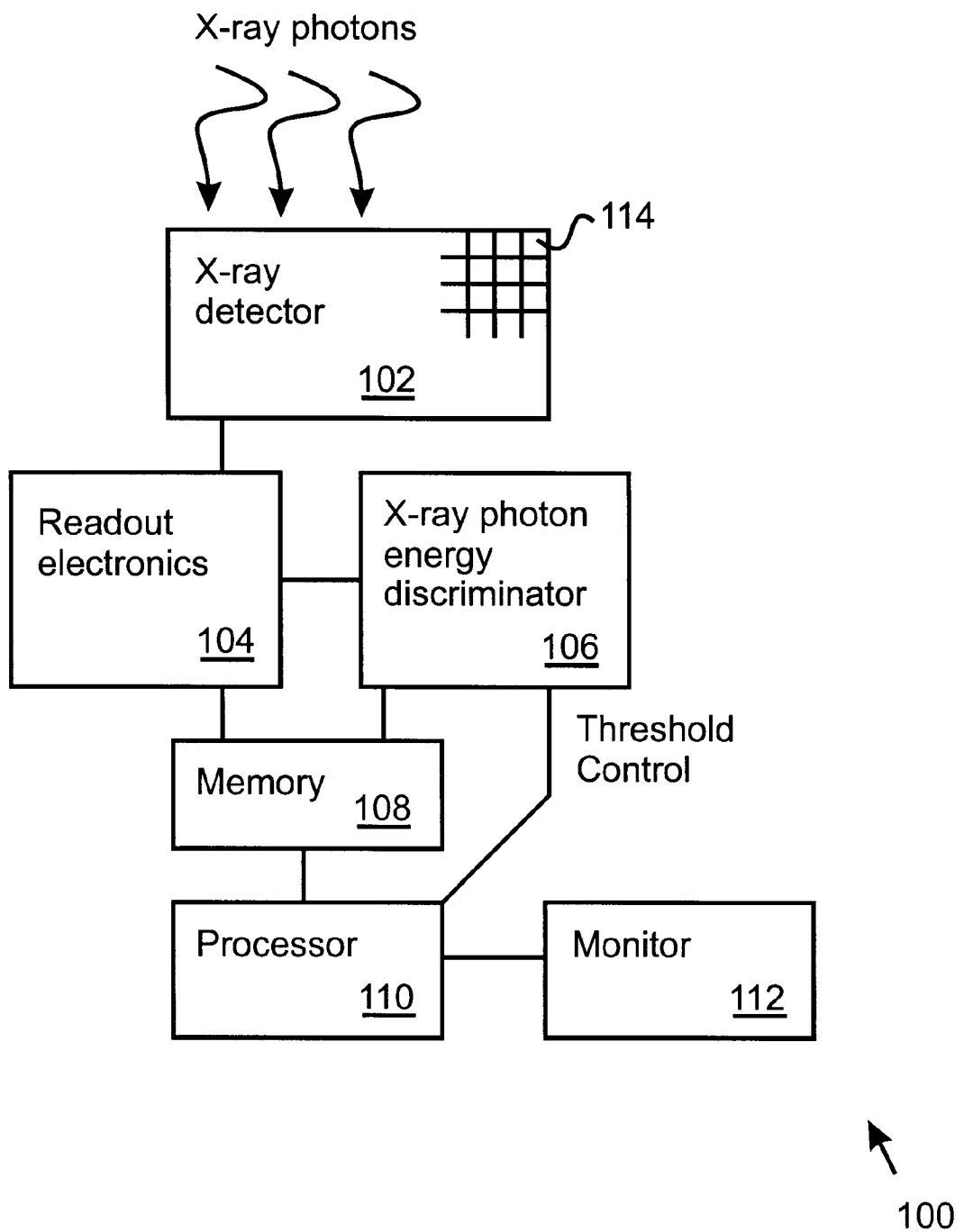
FIG. 1 illustrates a block diagram of an X-ray imaging system.

Turning now to FIG. 1, that figure shows a block diagram of an X-ray imaging system 100. The X-ray imaging system 100 includes a X-ray detector 102 (comprised of numerous pixels 114), readout electronics 104, and an X-ray photon energy discriminator 106. Also included is a memory 108, a processor 110, and a monitor 112.

The X-ray detector 102 is a photon-counting detector which may be formed from a material such as Cadmium Zinc Telluride (CZT) that directly reacts with X-ray photons (i.e., without the need for an intermediary scintillator to convert the X-ray photons to optical photons). Such detectors are available, for example, from Radiation Monitoring Devices of Watertown, Mass. 02472 and eV Products of Saxsonburg Pa. 16056. Alternatively, the detector may consist of a scintillator coupled to a light sensitive detector. The X-ray detector 102 is preferably a pixilated device organized by rows, i, and columns, j, that provides, at each pixel(i,j) (e.g., the pixel 114), X-ray photon sensitive material. The charge levels on the pixels vary in accordance with the X-ray photon energy incident on the pixel. Charge levels beyond certain thresholds may be measured using the X-ray photon discriminator 106.

The readout electronics 104 are coupled to the X-ray detector 102 and control row and column activation. Thus, the readout electronics 104 couple each pixel in turn to the X-ray photon discriminator 106. The X-ray photon discriminator 106 counts photons incident on the X-ray detector 102 above and below selected energy thresholds as explained below. Suitable X-ray photon discriminators have been demonstrated by, for example, Cardiac Mariners of Los Gatos Calif. 95030.

Before an examination period (i.e., that period of time during which the ROI is exposed to X-ray photons), the processor 110 sets a preselected energy threshold for the X-ray photon discriminator 106 using the threshold control input shown in FIG. 1. During the examination period, the X-ray photon discriminator 106 works in conjunction with the readout electronics 104 to monitor (e.g., by detecting interaction of the X-ray photons with charge stored in a pixel) each pixel to count X-ray photons above the current energy threshold and to count X-ray photons below the current energy threshold. As a result, the processor 110 obtains a first energy photon count and a second energy photon count. Presently available X-ray photon discriminators may use counting rates of, for example, 200 KHz to 5 MHz (i.e., 5 million photons counted per second), though higher counting rates are also suitable.

It is noted that more than one energy threshold may be set. In other words and as one example, the processor 110 may set a first and a second energy threshold. A count of the number of photons below the first energy threshold forms a first energy photon count, the number of photons above the first energy threshold and below the second energy threshold forms a second energy photon count, and the number of photons above the second energy threshold forms a third energy photon count. Each energy photon count may be stored in memory as examination data and used to produce an image as described below.

The processor 110 may also, during or after the examination period, readout from the X-ray photon discriminator 106 into the memory 108 the photon counts for each energy level and each pixel. In other words, the memory 108 stores as examination data a histogram of photon counts n(i,j,E) where (i,j) represents a pixel on the X-ray detector 102 and E represents individual energy thresholds as selected by the processor 110 during the examination period.

Once the examination data are present in the memory 108, the processor may apply any desired image processing technique to the examination data to produce an image for the display 112. Preferably, however, the processor 110 applies an energy dependent algorithm that operates on the energy dependence of the examination data to create a resultant image in which structures that are not of interest are eliminated. The resultant image may be referred to, for example, as a bone-canceled image (when bone structure is eliminated) or as a soft-tissue canceled image (when soft-tissue structure is eliminated). By removing undesired objects that overlie materials of interest, the diagnostic usefulness of the image is improved.

Examples of energy dependent algorithms are described in the literature and include, for example, dual-energy methods. In dual-energy imaging it is desired to increase the contrast to noise ratio of the object of interest while eliminating objects that are not of interest. As an illustrative example, consider bone cancellation imaging, which is used to remove bone from an image so that soft tissue contrast may be viewed without interference from bony structures. The procedure used is to first obtain low and high energy images of a calibration phantom including known thicknesses of basis materials, for example acrylic and aluminum. Calibration images are used to compute the relationship between the log of signal in the high and low energy images and thicknesses of the basis materials.

Next, high and low energy images are obtained in an X-ray examination of a patient. The images are combined to form images of equivalent thicknesses of the two basis materials by taking logs of the images and using the previously determined relationships between log of signal and basis material thickness. Finally, the basis images are linearly combined to form an image that cancels bone.

The contrast to noise in the final image depends sensitively on the energies used to form the high and low average images. In previous methods, the energies used to form these two images could not be optimized. In the stacked detector technique, the two energy spectra consist of the energies that happen to be absorbed in the front and rear detectors. There is typically a great deal of overlap between these spectra because the only way to get significant separation is to place a large amount of filtration between the two detectors. The filtration, however, causes the signal in the rear detector to be reduced. In the two-exposure technique, the energy separation between the two spectra can be increased, but two exposures are required with the associated aforementioned problems.

The present technique uses a single exposure and provides two or more photon energy counts. Any desired combination of energies may then be used to form the low and high energy images. The energy content of each image may then be optimized to afford maximum spectral separation.

A set of equations that describe the present technique follow:

$$O = \alpha * A + \beta * B$$

where $$A = \sum_{i,j=0}^{m} a_{ij} L^i H^j$$

$$B = \sum_{i,j=0}^{m} b_{ij} L^i H^j$$

and $L = -\log(I_{low})$ $H = -\log(I_{high})$ where, i and j are pixel coordinates, L is the negative of the log of the normalized low energy image $I_{low}$, H is the negative of the log of the normalized high energy image $I_{high}$, $\alpha$ and $\beta$ are coefficients which are adjusted to create the desired type of output image (e.g. bone-cancelled, soft-tissue-cancelled and the like), $I_{low}$ and $I_{high}$ are the low and high energy images, normalized by the signal measured without any material present, $a_{ij}$ and $b_{ij}$ are the combination coefficients obtained during the calibration procedure, A and B are the equivalent thicknesses of the basis materials, and O is the output image. As noted above, $I_{low}$ and $I_{high}$ are the images obtained with photons above and below the single energy threshold. When multiple thresholds are used, then $I_{low}$ and $I_{high}$ are formed by combining the signals from different energy bins (i.e., photon energy counts).

Figure 2:
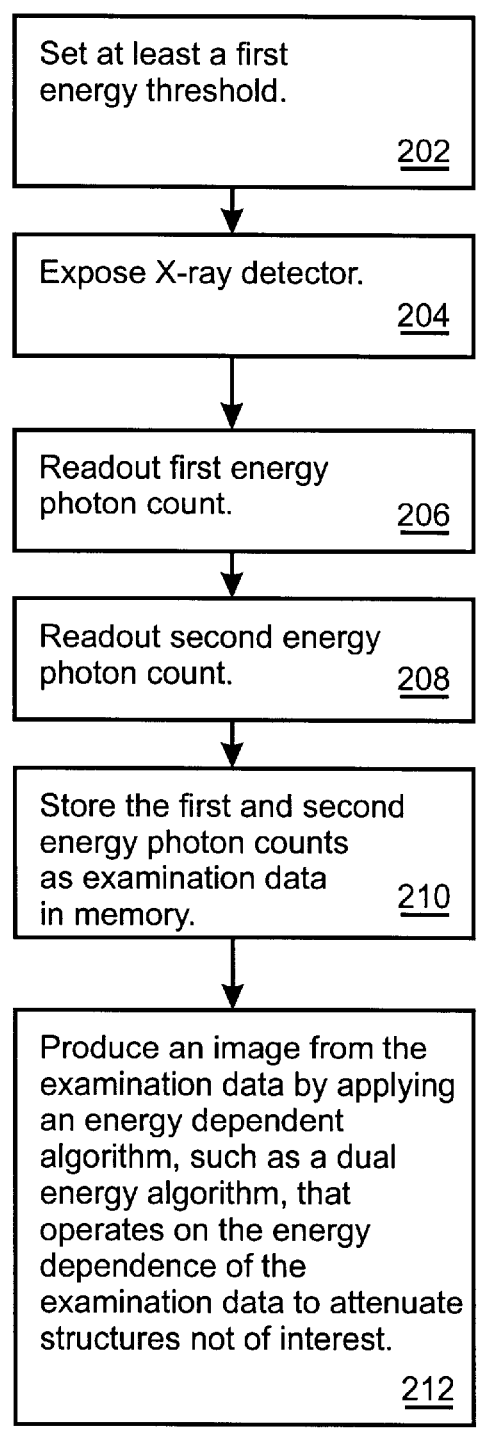
FIG. 2 shows a high level flow diagram of the steps executed by the X-ray imaging system to produce images, including steps executed in software by the X-ray imaging system processor.

Turning now to FIG. 2, that figure illustrates a high level flow diagram of the processing that occurs in the X-ray imaging system 100. Starting at step 202, the X-ray imaging system 100 sets at least one energy threshold (step 202), after which the X-ray imaging system 100 exposes the X-ray detector 102 to X-rays (step 204). Subsequently, the processor 110 allows the X-ray photon discriminator 106 to produce at leas t a first energy photon count (read out at step 206) of the number of photons above the energy threshold and a second energy photon count (read out at step 208) of the number of photons below the energy threshold.

Subsequently, at step 210, the X-ray imaging system 100 stores the first and second energy photon counts as examination data in the memory 108. Having the examination data, the processor 110 may then produce an image from the examination data at step 212. As noted above, the processor 110 preferably applies an energy dependent algorithm, such as a dual-energy image processing algorithm. The X-ray imaging system 100 then displays the image on the monitor 112.

Figure 3:
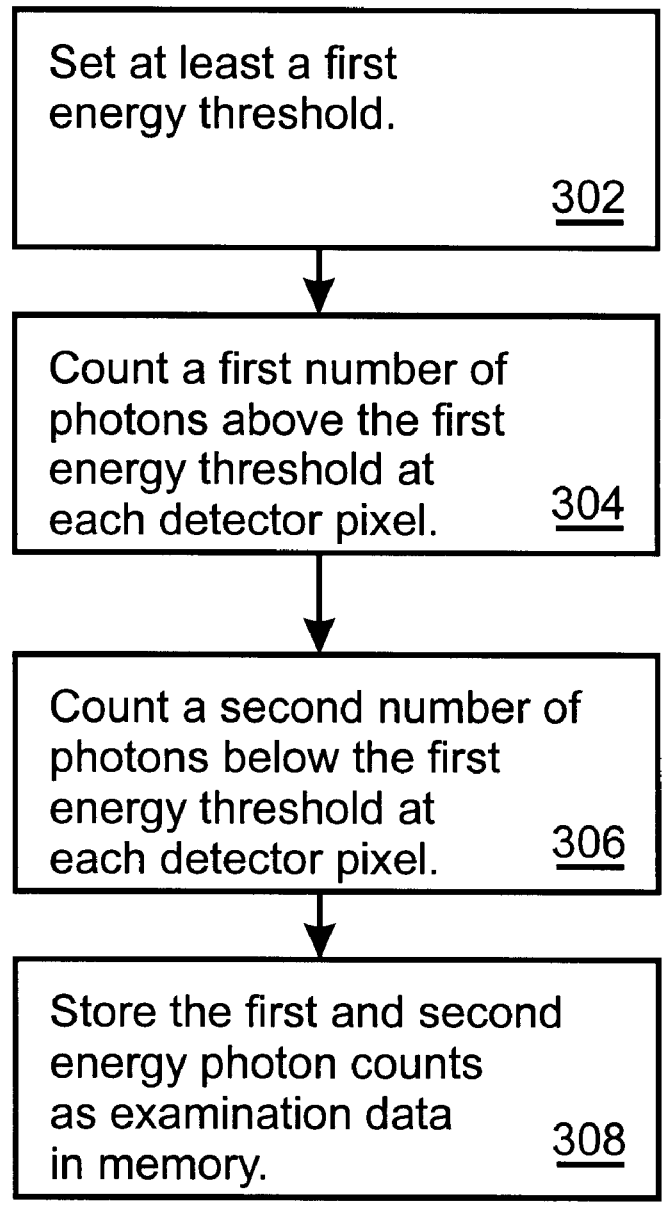
FIG. 3 illustrates a method for creating a histogram of X-ray photon energy.

Turning next to FIG. 3, that figure illustrates a method 300 for creating a histogram of X-ray photon energy. First, the X-ray imaging system 100 sets at least one energy threshold (step 302). Subsequently, the X-ray photon energy discriminator 106 counts a first number of photons above the first energy threshold (step 304) and counts a second number of photons below the first energy threshold (step 306). At step 308, the first and second energy photon counts are stored in memory as examination data.

Figure 4:
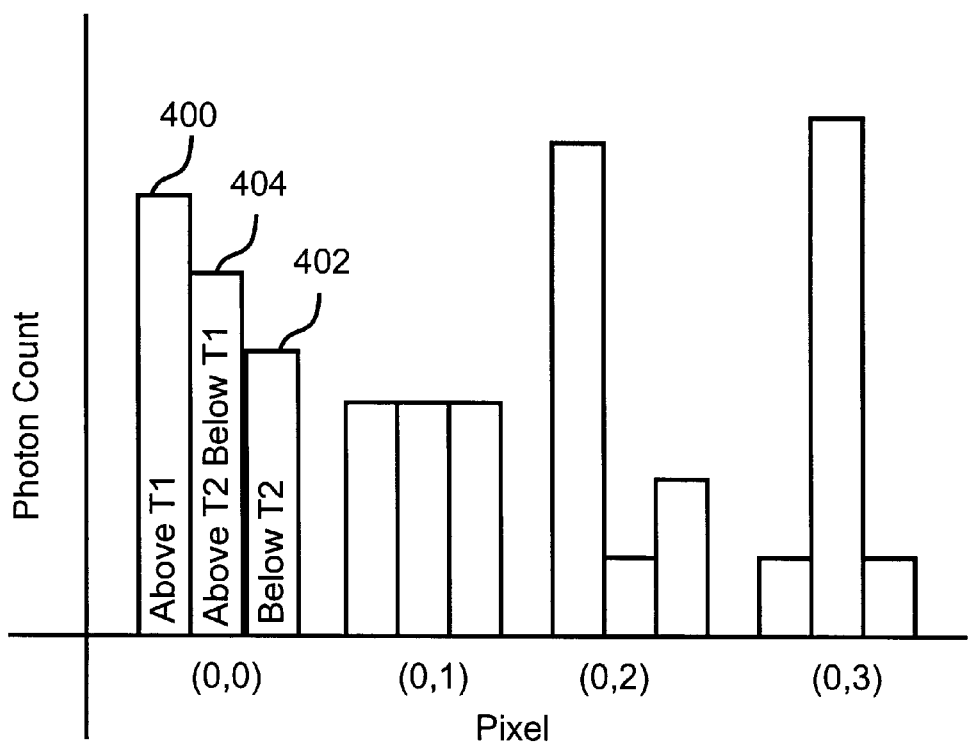
FIG. 4 shows a representative histogram for two energy thresholds T1 and T2.

FIG. 4 shows a representative histogram 400 for two energy thresholds T1 and T2. Four of the man y pixels that make up the X-ray detector 102 are indicated at (0,0), (0,1), (0,2), and (0,3). The histogram 400 includes a photon count for the number of photons at each pixel above the energy threshold T1 (e.g., the photon count 400), and a photon count for the number of photons below the energy threshold T2 (e.g., the photon count 402), as well as a photon count for the number of photons between the threshold T1 and T2 (e.g., the photon count 404).

Thus, the present X-ray imaging system and method counts photons above and below at least one energy threshold during the course of a single examination. In comparison with prior dual-energy imaging systems, the present system and method does not require the extra cost and complexity of stacked detector arrangements. Nor is the present system and method susceptible to patient movement between exposures. Rather, the present system and method captures the examination data needed for energy dependent image processing without exposing the patient to repeated X-ray doses.

While the invention has been described with reference to its preferred embodiments, it will be understood by those skilled in the art that various changes may be made and equivalents may be substituted without departing from the scope of the invention. In addition, many modifications may be made to adapt a particular situation or material to the teachings of the invention without departing from its scope. For example, the energy thresholds may be set above and below an expected material k-edge as an aid to identifying the material. Furthermore, by using only photon counts for energy levels between two closely spaced thresholds, the examination data may be processed to form a quasi-monoenergetic image, if desired. Therefore, it is intended that the invention not be limited to the particular embodiment disclosed, but that the invention will include all embodiments falling within the scope of the appended claims.

What is claimed is:

1. In an X-ray imaging system, a method for creating a histogram of X-ray photon energy, the method comprising:

setting a variable energy threshold of an X-ray photon energy discriminator to a first energy threshold prior to an examination;

counting, with the X-ray photon energy discriminator, a first number of photons above the first energy threshold incident on a detector;

counting, with the X-ray photon energy discriminator, a second number of photons below the first energy threshold incident on the detector; and storing the first number of photons and the second number of photons counted at a plurality of detector pixels.

2. The method of claim 1, further comprising the steps of setting a second energy threshold prior to examination, counting, with the X-ray photon energy discriminator, an additional number of photons below the first energy threshold and above the second energy threshold, and storing the additional number of photons, and wherein counting the second number of photons comprises counting a second number of photons below the second energy threshold.

3. The method of claim 1, wherein storing comprises storing the first number of photons and the second number of photons in a memory coupled to the X-ray photon energy discriminator.

4. In an X-ray imaging system, a method for X-ray photon energy dependent imaging of a region of interest, the method comprising:

setting a first energy threshold in an X-ray energy photon discriminator prior to an examination period;

exposing an X-ray detector, coupled to the X-ray energy photon discriminator, to X-ray photons during the examination period;

reading out a first energy photon count of photons above the first energy threshold from the X-ray detector;

reading out a second energy photon count of photons below the first energy threshold from the X-ray detector;

storing the first energy photon count and the second energy photon count in a memory as examination data; and producing an image using the examination data.

5. The method of claim 4, wherein the exposing step comprises exposing a direct conversion X-ray detector to X-ray photons during the examination period.

6. The method of claim 4, further comprising constructing a histogram from the examination data.

7. The method of claim 6, wherein producing comprises producing the image using an energy dependent algorithm.

8. The method of claim 6, wherein producing comprises producing the image using a dual-energy energy dependent algorithm.

9. The method of claim 4, further comprising setting a second energy threshold in the X-ray energy photon discriminator;

reading out, with the X-ray photon energy discriminator, an additional energy photon count of photons below the first energy threshold and above the second energy threshold, wherein reading out the second number of photons comprises reading out a second number of photons below the second energy threshold;

the storing step further comprising storing the first energy photon count, the second energy photon count, and each additional energy photon count in the memory as the examination data.

10. The method of claim 9, further comprising constructing a histogram from the examination data.

11. The method of claim 10, wherein producing comprises producing the image using an energy dependent algorithm.

12. The method of claim 10, wherein producing comprises producing at least one of a bone cancelled and tissue cancelled image.

13. An X-ray imaging system adapted for X-ray photon dependent energy imaging of a region of interest, the imaging system comprising:

a pixilated X-ray detector responsive to X-ray photons during an examination period;

an X-ray photon energy discriminator coupled to the X-ray detector, the discriminator having at least one energy threshold;

a memory coupled to a processor, the memory storing instructions for execution by the processor for setting the energy threshold prior to the examination period to a first energy threshold, reading out a first energy photon count of photons above the first energy threshold, reading out a second energy photon count of photons below the first energy threshold, storing the first energy photon count and the second energy photon count in a memory as examination data, and producing an image using the examination data.

14. The X-ray imaging system of claim 13, wherein the X-ray detector is a direct conversion X-ray detector.

15. The X-ray imaging system of claim 14, wherein the X-ray detector is a Cadmium Zinc Telluride X-ray detector.

16. The X-ray imaging system of claim 13, wherein the instructions for producing an image apply a dual-energy image processing algorithm to the examination data.

17. The X-ray imaging system of claim 13, wherein the instructions for producing an image apply an energy dependent algorithm to the examination data.

18. The X-ray imaging system of claim 13, wherein the instructions further comprise instructions for:

setting a second energy threshold in the X-ray energy photon discriminator, reading out an additional energy photon count of photons below the first energy threshold and above the second energy threshold, wherein the second number of photons comprises a count of the number of photons below the second energy threshold.

19. The X-ray imaging system of claim 17, wherein the image is a bone-cancelled image.

20. The X-ray imaging system of claim 19, wherein the image is a soft-tissue cancelled image.

* * * * *